United States Patent [19]

Ritts, Jr.

[11] Patent Number: 4,647,535

[45] Date of Patent: Mar. 3, 1987

[54] HUMAN NONSECRETORY PLASMACYTOID CELL LINE

[75] Inventor: Roy E. Ritts, Jr., Rochester, Minn.

[73] Assignee: Research Corporation, New York, N.Y.

[21] Appl. No.: 416,587

[22] Filed: Sep. 10, 1982

Related U.S. Application Data

[63] Continuation-in-part of Ser. No. 292,277, Aug. 21, 1981, Pat. No. 4,434,230.

[51] Int. Cl.$^4$ ............................................. C12N 5/00
[52] U.S. Cl. .................................. 435/172.2; 435/68; 435/240; 435/948; 530/387; 935/100; 935/106
[58] Field of Search .................. 935/90, 93, 108, 100, 935/106; 435/172.2, 240, 241, 948, 68; 436/548; 530/387

[56] References Cited

U.S. PATENT DOCUMENTS 4,434,230  2/1984  Ritts, Jr. ............................. 435/241

*Primary Examiner*—Sidney Marantz
*Attorney, Agent, or Firm*—Scully, Scott, Murphy & Presser

[57] ABSTRACT

A human non-secretory plasmacytoid HPRT$^-$ mutant continuous cell line, can be used for the preparation of human-human hybridomas with human B-lymphocytes and separation of the resulting hybridomas from the plasmacytoma cell line by growth in HAT media, or by fluorescence activated cell sorting, or both.

9 Claims, No Drawings

4,647,535

HUMAN NONSECRETORY PLASMACYTOID CELL LINE

This application is a continuation-in-part of U.S. patent application Ser. No. 292,277 filed Aug. 21, 1981, now U.S. Pat. No. 4,434,230.

BACKGROUND OF THE INVENTION

1. Field of the Invention

The present invention relates to a human cell line useful for the preparation of monoclonal antibody-secreting human-human hybridomas.

2. Description of the Prior Art

The preparation of hybridoma cell lines derived by fusing a mouse myeloma cell line and mouse B-lymphocytes sensitized against a given antigen is by now well known in the art. For example, based on the original work by Kohler, G. and Milstein, C. (Nature 256: 495–497 (1975); European Journal of Immunology, Vol. 6, pp. 511–519 (1976), see also Milstein, C.: "Monoclonal Antibodies", Scientific American, Vol. 243: 66–74 (1980)), Koprowski et al, in U.S. Pat. No. 4,172,124, prepared somatic cell hybrids between hypoxanthine phosphoribosyl transferase (HPRT) deficient (HPRT$^-$) cells and spleen or lymph cells derived from a mouse previously primed with tumor cells. Koprowski et al, in U.S. Pat. No. 4,196,265, prepared continuous cell lines of genetically stable fused cell hybrids capable of producing large amounts of monoclonal antibodies against specific viruses and their antigenic determinants. The cell lines of Koprowski et al '265 are fused cell hybrids between viral antibody producing cells and myeloma cells. Wands et al, U.S. Pat. No. 4,271,145, disclose cell lines for producing monoclonal antibodies to hepatitis virus established by immunizing animal lymphocytes with hepatitis antigen to form antibody-producing cells which are then fused with myeloma cells.

The aforementioned prior art references, however, disclose only hybridomas derived from non-human (in most cases mouse) myeloma and non-human lymphocyte cells.

It has been recognized (see for example Milstein, C., Scientific American supra, at 74) that for a variety of therapeutic applications, antibodies derived from human lymphocytes rather than from the mouse or the rat would be much more desirable. Although chimeric hybridomas have been obtained by fusing mouse myeloma cells with human IgG-producing cells (Levy, R. and Dilley, J., Proceedings of the National Academy of Sciences U.S.A., 75:2411–2415 (1978)), these hybrids tend to be unstable due to the fact that when human cells are fused with non-human cells there is a rapid preferential loss of human chromosomes from the resulting interspecific hybrid cells.

In fact, in October, 1980, Milstein (Scientific American, supra) stated that "so far, the search for a suitable human myeloma line that can be cultured and fused to make an intraspecific hybrid has not borne fruit".

There exists a need therefore for a successful method for preparing human-human hybridoma cell lines. This need would be fulfilled with the existence of an appropriate, long surviving, pure, continuous human cell line capable of being fused with human B-lymphocytes to produce said hybridoma lines.

SUMMARY OF THE INVENTION

It is therefore an object of the invention to provide a human cell line useful for the preparation of human-human hybridomas by fusion of said cell line with human B-lymphocytes.

It is another object of the invention to provide a human plasmacytoma cell line useful for the preparation of human-human hybridomas, which plasmacytoma cell line does not secrete immunoglobulins.

Still another object of the invention is to provide a method of preparing human-human hybridomas.

Yet another object of the invention is to provide a method of preparing human-human hybridomas which utilizes an HAT selection technique and/or the absence of surface membrane immunoglobulin receptors for the isolation of the hybridoma cell line.

These and other objects of the invention as will hereinafter become more readily apparent have been attained by providing:

A biologically pure culture of an HPRT$^-$, continuous, human, non-secretory plasmacytoid cell line having ATCC deposit #CRL8147, as well as clones and subclones thereof.

Another object of the invention has been attained by providing:

A method of producing human-human hybridomas which comprises:

fusing a human B-lymphocyte with the aforementioned HPRT$^-$ non-secretory human, continuous plasmacytoma cell line to form monoclonal antibody-producing hybridoma.

Still another object of the invention has been attained by providing human-human hybridomas and monoclonal antibodies derived therefrom.

DESCRIPTION OF THE PREFERRED EMBODIMENTS

In U.S. application Ser. No. 292,277, filed Aug. 12, 1981 at the U.S. Patent and Trademark Office, entitled "Human Nonsecretory Plasmacytoid Cell Line", now U.S. Pat. No. 4,434,230 (herein fully incorporated by reference), the present inventor disclosed a human plasmacytoma cell line which does not secrete immunoglobulins, which line can be cultured continuously in cell culture, which is biologically pure, free of mycoplasma, and which can be fused with human B-lymphocytes to prepare human-human hybridomas. The discovery of this plasmacytoma cell line (hereinafter "parent line") opened up the possibility of preparing stable, continuous, human-human hybridomas.

Since the parent plasmacytoma cell line of Ser. No. 292,277 does not secrete immunoglobulins, and the hybridomas do, the parent line, in addition, allows for the selective separation of hybridomas from the plasmacytoma by taking advantage of this property. It was also disclosed in Ser. No. 292,277 that the parent plasmacytoma cell line grows well in an atmosphere of 3–5% $CO_2$ but is 85–95% killed in an environment which is 9–11% $CO_2$ or higher. This provided for yet another method of separating the hybridomas from the plasmacytoma, since the former are routinely grown in 10% $CO_2$. Finally, Ser. No. 292,277 also generally disclosed that HPRT deficient (HPRT$^-$) mutants of the parent plasmacytoma cell line could in principle be prepared, although no details were provided. The HPRT negative mutants, therefore, were suggested as providing still a third method of separating the (mutant) plasmacytoma cell line from the hybridomas, by using the well known HAT selection media.

The present invention is related to the detailed preparation, isolation, identification and use of HPRT deficient mutants of the parent plasmacytoma cell line of Ser. No. 292,277, as well as fusions thereof with human B cells to produce monoclonal antibodies.

The prior art method of generally securing HPRT-deficient mutants has been to isolate and grow cells surviving in media containing 6-thioguanine (6-THG) or 8-azaguanine (8-AZG) up to 15–30 μg/ml. This was reported to be successful with a human secretory plasma cell (U266) by Olsson and Kaplan, Proc. Nat. Acad. Sci. USA, 77:5429–5431 (1980), but could not be duplicated in five experiments with the parent line of Ser. No. 292,277.

Therefore, different approaches are used in the present invention to yield HPRT-deficient phenotypic mutants of the parent line. Following the approach of Okada et al (*Proc. Nat. Acad. Sci. USA*, 78:7717–7721 (1981)) parent line cells are dispersed in well tissue culture dishes in tissue culture medium (TC) containing 2 μM of 8-AZG with increasing concentrations of 3.5 μM 8-AZG increments being substituted in fresh media every other day, until a final concentration of 100 μM (~15 μg/ml) is achieved.

A 20–25% decrease in the viability of the parent line is observed within the initial 18–24 hour period following each successively higher concentration of 8-AZG, but a comparable or greater number of cells from the surviving dividing cells are routinely noted just before the next addition of 8-AZG at 48 hours. Consequently, the cell density remains relatively constant at starting concentrations until 16–22 μM concentrations of 8-AZG are reached, at which time cell viability is more severely affected and cell density decreases. At this period, 48 hour cell replication of 8-AZG resistant cells is not capable of maintaining the initial density to replace those killed by 8-AZG, but despite this phenomenon 8-AZG resistant surviving cells are obtained by day 60 and are resistant to 100 μM 8-AZG.

Another approach to obtaining the mutant line is to place parent line cells in Hank's balanced TC fluid containing about $10^{-2}$ M of ethylmethane sulfonate (EMS) for one hour, followed by four washes with RPMI 1640 and a fifth wash with the same TC media plus 20% fetal calf serum (FCS). This procedure yields 75% viable mutagenized cells which are thence exposed to 8-AZG as in the previous (first) approach, or are exposed first to 10 μg/ml of 8-AZG, then surviving cells sequentially being incubated with 15μg/ml and thence with 20μg/ml of 8-AZG.

8-AZG resistant (to ~20 μg/ml) surviving parent cells obtained by any of these techniques are then cloned out by limiting dilution and a number of those having a generation time <30 hours in 100 μM of 8-AZG are retained for comparison with passage 2 and 152 of the original parent cell line.

As all of the cytological, surface membrane, immunological and secretory defect characteristics of the HPRT− mutants are identical to the parent, except for minor differences in generation times, ability to grow in suspension cultures and inability to grow in HAT, three resistant clones from the mutagenized approach and three resistant clones from the non-mutagenized incremental exposure to increasing amounts of 8-AZG were retained for further study, and the rest were discarded.

The retained lines were termed respectively MC/MNS-1, -2 and -3, and MC/ZNS-1, -2 and -3.

Detailed study of these six derived HPRT-deficient phenotypic lines has revealed no differences from the parent cell line in their light or electron microscopic morphology, karyotype, immunological characteristics or membrane markers. Additional experiments on growth characteristics have revealed some minor differences in these lines, each of which may lend itself toward specialized application. These characteristics are compared with the parent cell line in Table 1 below.

TABLE 1

| | Parent | MNS-1 | MNS-2 | MNS-3 | ZNS-1,-2,-3 |
|---|---|---|---|---|---|
| Generation time | 19.2 h | 26 h | 18.1 h | 18 h | 19.8 |
| % Cells with cytoplasmic IgG | 15–18% | 12% | 25% | 10% | 10–13% |
| Surface membrane IgG | 0 | 0 | 0 | 0 | 0 |
| Growth in spinner culture | ++++ | + | +++ | ++++ | +++ |
| Growth in flasks | ++++ | +++ | ++++++++ | ++++ | ++++ |
| Karyotype | 46 XY | 46 XY | 46 XY | 46 XY | 46 XY |
| Sensitivity to 11% CO₂ | ++++ | + | ++ | ++ | +++ |
| HAT sensitivity | 0 | + | + | + | + |

Ia, β2- microglobulin, B1 surface characteristics, morphology-same in all

The fusion efficiencies of the parent, MNS-2 and MNS-3 with human B cells are the same, MNS-1 not being as useful for hybridization because of its relatively slower generation time. ZNS-1, -2 and -3 have fusion efficiencies comparable to MNS-2 and -3.

The six HPRT− phenotypes are maintained in continuing serial passage and are kept in RPMI 1640 with 20 μg/ml 8-AZG. No feeder layers are required.

Long-term culture without 8-AZG has not been performed to assess the possible frequency of reversion to the parental HPRT+ phenotype, as this information has no relevance for its use in hybridization, the parental line (HPRT+) then being so employed. No significant differences can be noted attributable to the method of deriving these three HPRT− lines; i.e., MNS-3 which was mutagenized and, thence, exposed to increasing amounts of 8-AZG is essentially the same as MNS-1 and -2, excepting the minor differences in the number of cells bearing cIgG, which is also seen between MNS-1 and -2, as well as the three 2 NS clones.

MNS-2 line was deposited at the ATCC on July 28, 1982, with access number #CRL8147 . MNS-2 is deemed the best of the six mutants by virtue of its 18 hr. generation time and 25% cells bearing cIg.

Two properties of the cell lines of the invention can be used advantageously to prepare and selectively separate hybridoma cell lines: (1) The cell lines are not secretory cell lines producing IgG or IgM, and (2) The cell lines are HAT sensitive.

(1) Basic hybridoma technology requires that the immortalized cell line, (e.g., the cell line of the invention), be separated from the fused cell or hybridoma, which becomes immortalized. The antibody-making B-cell that does not fuse is not a problem. Being normal, it dies in 7–14 days in culture. The basic problem is that the immortal cell line grows orders of magnitude faster than the initially fragile and very slowly replicating fused cell, and by sheer numerical advantage makes it near impossible to rescue, find or isolate the hybrid; or the immortal cell line simply overgrows and kills the hybrid. Because the fusable cell lines available to date are "myeloma" cells and thus secrete IgG, IgM (or rarely IgA) just as the hybrids do, the hybrids and the original cell line cannot be distinguished from each other if they secrete the same class of Ig. Even if the hybridoma-secreted Ig class were dissimilar from the parental line's Ig, it is extremely difficult to rescue the small numbers of delicate hybridoma cells. However, since the plasmacytoma cell line HPRT− mutants of the invention are not secretory cells elaborating any Ig's, it is possible to fuse the cell lines of the invention with a human B cell and separate the plasmacytoma mutants immediately after fusion by a fluorescence-activated cell sorter (for example FACS IV ®), since only the monoclonal Ig and/or antibody-generating cells and the B cells will have receptors for IgG or M on their cell membranes. The cell lines of the invention do not. Further, the cell line of the invention cannot be made to secrete Ig by conventional means reported in the literature to enhance secretion, or by placing them in hybridoma media. polyethylene glycol or HAT media as employed for fusion.

Alternatively and preferably, one can wait for 2 weeks until the B-cell has died and then separate the plasmacytoma from the hybridoma by cell sorting. Although there may be practical problems in carrying this method out to a successful completion, because of the low fusion frequency (very few hybrids are present in the reaction mixture and are therefore not easily separated by the FACS from the several millions of cells of the plasmacytoma of the invention), fluorescence activated cell sorting following incubation in 10-20% $CO_2$ (which is toxic to the HPRT+ parental line) is clearly a preferred method of separation envisioned by the present inventor. With highly discriminating and highly sensitive FACS ® it is possible to readily separate the hybrid from the plasmacytoma.

(2) The primary useful property of the plasmacytoma HPRT− mutants of the invention is that they are HAT sensitive, and can thus be used in the conventional methodology routinely used in generating hybridomas murine. They will not grow in aminopterin-containing medium because of their inability to synthesize purines from thymidine and hypoxanthine. The selection medium used to allow only growth of hybrids is composed of about $1 \times 10^{-4}$ M hypoxanthine, $4 \times 10^{-7}$ M aminopterin and $1.6 \times 10^{-5}$ M thymidine.

The fusion mixture can be grown in HAT-containing culture medium immediately after the fusion or 24 hours later. The feeding schedules usually entail obligatory feeding of HAT medium on days 1, 7 and 10 (or more frequently if there is rapid growth), and then growth in either regular medium or hypoxanthine, thymidine containing medium, as the mutants have then died and only the hybrid fused cells are viable.

Fusion of the plasmacytoma HPRT− mutant can be carried out by any of the well known fusion techniques available to the art (see for example the Koprowski et al patents and the Wands et al patent cited supra). For example, human lymphocytes are stimulated or immunized in vitro or in vivo by preparation of an antigen. The antigen may be one which causes infections in humans, (or fractions of said antigen) such as viral antigens, bacterial antigens, and the like, e.g., rubella, roseola, hepatitis B surface antigen, hepatitis BE antigen, EBV, SV 40 tumor antigen and the like. The antigen may also be tumor-associated or cell surface associated. Administration of the antigen can be carried out intravenously or subcutaneously or both, depending on the nature of the agent. The dosage and route follow commonly accepted clinical procedures.

Alternatively and preferably the B-cells are obtained from a patient with a given disease or immunity and who has a high antibody titer to a desired immunogen. Healthy individuals may have high antibody titers to a desired immunogen or can be immunized or given an "booster" injection. B-cells can be obtained from the spleen (rarely, and only when such is indicated clinically), from peripheral blood of the human subject, which is preferred as the source (peripheral blood contains about 20% B cells, which can be separated by standard methodology), or from the lymph nodes. Blood is preferred since it can be routinely obtained in sterile fashion, is easily testable for sterility and the presence of antibodies and is normally sterile, whereas the spleen is frequently contaminated with commensal organisms and can only be acquired by invasive techniques.

Fusion of the human B-cells with the plasmacytoma mutants of the invention can be carried out following the method of Kenett et al used in murine systems (Curr. Topics Microbiological Immunol. 81:77, 1978), but after activation or sensitization of B-cells. Plasmacytoma mutant cells are mixed with B-cells and polyethylene glycol (PEG) added after the original medium is drained. After incubation with PEG for a short period of time, (6-9 minutes, 20° C. without centrifugation—unlike the Kenett report) cells are separated, resuspended in hybridoma medium, plated and grown in 5-11% $CO_2$ atmosphere depending upon the $CO_2$ requirements of the hybrids. Separation can then be carried out by the FACS ® method (adding appropriately fluorescent labeled antibodies) or by incubating the cells in HAT medium. The microtiter wells are screened for positive growth and human Ig production for 10-30 days following the fusion, and hybridoma cell lines can be selected for cloning from, first, those colonies secreting human Ig and, thence, the positively identified monoclonal antibody secretors. Cloning can be carried out by conventional techniques, such as limiting dilution plating or in methyl cellulose (1% in hybridoma medium).

In sum, the cell line is composed of monoclonal, non-secretory plasmacytoid cells; in its growth cycle about 10-25% of cells are synthesizing IgG1/κ (detected only in the cytoplasm) but are not secreting either heavy or light chains. Because of its stability, viability and other characteristics (it is mycoplasma free), it can be useful not only for the preparation of hybridomas and their attendant monoclonal antibodies, but also for the study of its secretory defects.

Further, any human Ig generated by the hybrids is thus an in vitro produced monoclonal immunoglobulin, and may well be satisfactory for replacement therapy in individuals with congenital or acquired IgG deficiency, since it is free of microorganisms, particularly the virus causing hepatitis, which frequently contaminates sera collected from human donors.

The human monoclonal antibodies obtained from the hybridomas can be used in passive immunization to treat such infections as measles, rubella, german measles, etc., without fear of immunizing the patient to a foreign serum. They can be used in tumor therapy, as for example in the targetting of toxic drugs: antibodies generated to the tissues of a particular organ or to putative specific or known associated tumor antigens can be attached to the drug molecules to concentrate the drug's effect. Alternatively, it may be possible to produce antitumor antibodies that will themselves attack tumor cells.

Having now generally described this invention, the same will be better understood by reference to specific examples and procedures which are included herein for purposes of illustration only and are not intended to be limiting of the invention unless specified.

EXAMPLE 1

$2 \times 10^7$ parent cells/ml were dispensed in twenty-four 2 ml well tissue culture dishes in RPMI 1640 tissue culture medium (TC) containing 2 μM of 8-AZG with increasing concentrations of 3.5 μM 8-AZG increments being substituted in fresh media every other day until a final concentration of 100 μM (~15 μg/ml) was achieved. (When growth at this concentration is achieved, the cultures are then transferred to 20μg/ml 8-AZG, and successive passages may be made routinely after the first 1-3 days of stabilization.)

A 20-25% decrease in the viability of the parent line was observed within the initial 18-24 hour period following each successively higher concentration of 8-AZG, but a comparable or greater number of cells from the surviving dividing cells were routinely noted just before the next addition of 8-AZG at 48 hours. Consequently, the cell density remained relatively constant at $\sim 2 \times 10^7$/ml until 16-22 μM concentration of 8-AZG were reached, at which time cell viability was more severely affected and cell density decreased. At this period, 48 hour cell replication of 8-AZG resistant cells was not capable of maintaining the initial density to replace those killed by 8-AZG but, despite this phenomenon, 8-AZG resistant surviving cells were obtained by day 60 and were resistant to 100 μM 8-AZG, and thence over a period of 7-10 days gradually increased viability, assuring generation times of 18-24 hrs. During this period, cell density of $0.5 \times 1 \times 10^7$ cells/ml of medium in 2-4 ml volume is attendant with rapid recovery while 5-30 ml volumes, irrespective of density, required a longer period (1-2 weeks) for stabilization.

Note: Growing of MNS-2 Cells From Frozen Samples
Preparation of Culture Medium 1. 8-azaguanine stock solution. Two hundred mg of 8-azaguanine (AZA) are added to 90 ml of distilled water and stirred at room temperature for 60 minutes. Solution is not complete at this point. NaOH 0.2 N is then added dropwise and slowly, just until solution is completed (pH 10.40), and then the mixture is brought up to 100 ml with dH$_2$O. One ml aliquots are prepared and stored frozen ($-20°$ C.) until used. When used, they are warmed at 37° C. for 15 minutes before added to the culture medium.

2. Culture medium. It is prepared by mixing the following 78 ml of RPMI 1640 medium, 20 ml of heat-inactivated (56° C. for 30 minutes) fetal calf serum, 1 ml of 200 mM L-glutamine, 1 ml of AZA stock solution (see above) and 200 μl of a 50mg/ml solution of gentamycin sulfate. The mixture is filtered through a 0.20 μm millipore unit (Nalge) and transferred to sterile glass bottles. Every batch of medium thus prepared is used within one week.

Thawing and Growing Cells

Cells are thawed by shaking a frozen vial inside a 37° C. waterbath until a very small piece of ice is left. The vial is immediately placed in an ice bath (4° C.), cracked open, its content transferred to a 17×100 mm round-bottom plastic tube followed by the dropwise addition of 5 ml of serumless RPMI 1640. The cells are gently mixed with a pipette and 5 ml more of the same medium are added. The mixture is spun at 450×G for 10 minutes at 4° C. The supernatant is discarded and the pellet tapped loose and resuspended in AZA-containing medium at a density of $5 \times 10^5$ cells/ml. One half of one ml of the cell suspension is placed in each well of a 24-cell culture dish and placed in a 37° C., 5% CO$_2$, 90% humidity atmosphere. When cell cultures show macroscopic clumping, and/or the supernatants turn acid (usually in the first 24-48 hrs), one half of one ml of fresh medium is added to each well. If clumps get too big (0.5 mm diameter) they are broken loose by pipetting back and forth. Thence, cultures are split into more wells when found to be acid or when showing intense clumping, in order to keep the cell density at $5 \times 10^5$ per ml. An alternative to splitting into several wells is to transfer the content of each small well to a larger well of a six-well culture dish, keeping the same cell density. If after two weeks the cells keep growing well in dishes (doubling every 20-24 hours and keeping ≧90% viable) they can be transferred from plates (regardless of the size of the well) to 75 cm$^2$ tissue culture flasks, seeding at a slightly lower density ($4 \times 10^5$ cells/ml) in a volume not to exceed 30 mls. Thereafter cells are counted, fed and reset at the same density every other day. In general, cells maintain better growth rates and viability when cultured in dishes than when kept in flasks.

EXAMPLE 2

$2 \times 10^7$–$2 \times 10^8$ parent line cells were placed in Hank's balanced TC fluid containing 10$^2$ M of ethylmethane sulfonate (EMS) for one hour followed by four washes with RPMI 1640 and a fifth wash with the same TC media plus 20% fetal calf serum (FCS): This procedure yielded 75% viable mutagenized cells which were thence exposed to 8-AZG as in Example 1 above.

EXAMPLE 3

8-AZG resistant (to 131 μM, 20 μg/ml) without using increasing concentration but isolated from repeated subculturing in 20 μM/ml 8-AZG were cloned out by limiting dilution and a number of those having a generation time <30 hours in 131 μM of 8-AZG were retained for comparison with passage 2 and 152 of the original parent line. As all of the cytological, surface membrane, immunological and the secretory defect characteristics were identical to the parent, three resistant clones (MNS-1, -2, -3) were retained for further study and the rest were discarded.

EXAMPLE 4

Anti-Rubella Monoclonal Antibody from a Human X Human Hybridoma

1. In vitro Sensitization with Attenuated Live Virus Vaccines.

Mononuclear Cells (MNC) from healthy male donor known to have high titers of circulating antibodies to measles (1:16 by immunofluorescence) and rubella (4.534 Rubizyme ® index) were obtained by gradient centrifugation on Ficoll-Hypaque ®. Cells thus obtained were placed in flat-bottom well microtiter dishes at a cell density of $1 \times 10^5$ cells/200 μl well with several dilutions of attenuated live measles or rubella virus vaccines [Merck, Sharp & Dhome; Lot #0237D and #1437E, respectively] ranging from 1:200 to 1:1,128,000 dilutions. After day 2, at daily intervals, a 50μl sample from all supernatants was harvested to be assayed for the presence of human immunoglobulin by enzyme-linked immunosorbent assay (ELISA), and the cells were incubated in the final 18 hrs with 0.125 μCi/well of 3H-thymidine (3H-TdR) [Sp. Act. 2.0 Ci/mM] to measure incorporation of the radioactive nucleoside to determine blast transformation. These experiments showed that a final dilution of 1:4000 (1 $TCID_{50}/2 \times 10^6$ cells) of the measles vaccine caused the highest 3H-TdR uptake by day five, as well as the highest amount of secreted immunoglobulin by day seven; a final dilution of 1:32,000 (1 $TCID_{50}/16.6 \times 10^6$ cells) of rubella vaccine gave optimum blastogenesis and Ig secretion on the same days as measles antigen.

Using these data as a guide, a new blood sample was obtained from the same donor and bulk cultures ($1 \times 10^6$ cells/ml in 75 cm² TC flasks) of his MNC with the predetermined optimal dilutions of each vaccine were made. Five days later (optimal for blast transformation and DNA synthesis and just prior to optimal Ig secretion) these cells were harvested for fusions without any further enrichment procedures. The cell preparations were >90% viable and ~20% of them were blastoid under phase contrast microscopy.

2. Human Myeloma Parental Cell

For the fusions, the 8-azaguanine resistant, HAT sensitive human myeloma cells (MNS-2) obtained after ethylmethane sulfonate mutagenesis of the human parent nonsecretory myeloma cells (see Ser. No. 292,277, ATCC #CRL 8083), and subsequent selection in 20 μg/ml of 8-azaguanine, were used. This cell line was kept in exponential growth (doubling time 21 hrs) prior to all the fusions and showed viability of >90% in all instances.

3. Hybridization Protocols

In all fusions, both parental cells were washed twice with serum-free RPMI 1640 culture medium, mixed at a ratio of 1 myeloma cell (MNS-2) to 3 normal mononuclear cells, pelleted and resuspended in 0.2 ml of prewarmed (37° C.) 30% polyethylene glycol (MW 1000). The reaction mixtures were kept in a 37° C. waterbath under gentle agitation for exactly six min after which 10 ml of prewarmed (20° C.) RPMI 1640 medium containing 10% fetal calf serum (FCS) were added dropwise. Cells were then pelleted and resuspended in RPMI 1640 medium containing 10% FCS, hypoxanthine (H) (13.6 μg/ml) and thymidine (T) (7.6 μg/ml) at a cell concentration of $5 \times 10^5$/ml. Onehalf cc cultures were incubated in 24-well flat-bottom culture dishes, since previous experience showed that lower cell densities resulted in failure of the hybridomas to grow.

Cultures were incubated at 37° C., 100% humidity and 5% $CO_2$ atmosphere since the resulting hybridomas are sensitive to higher percentages of $CO_2$, even though the 8-azaguanine resistant cells MNS-2 are less sensitive than ATCC #CRL 8083 in this respect, and hybridomas made with CRL 8083 are not sensitive to 10–11% $CO_2$. Indeed, this concentration of $CO_2$ is used to select the fusions with ATCC CRL 8083. Twenty-four hours after the fusion, one-half cc of culture medium containing the same amounts of H and T but twice the regular (0.18 g/ml) amount of aminopterin (A) was added to each culture. Thereafter the cultures were fed with HAT medium on a weekly basis by removing 0.55 cc of spent medium, and replacing it with the same amount of fresh medium. When cell growth became vigorous as judged by the decrease of pH and appearance of macroscopic clumps of cells, each culture was split into two 0.5 cc cultures, and fed with fresh HAT medium. HAT medium was used only for a total of three weeks, since it was previously established that in less than two weeks the MNS-2 cells die. HAT medium was, thence, replaced progressively by removing 0.5 cc of the spent medium and adding equal amounts of fresh hybridoma medium [Kennett. Monoclonal Antibodies, Plenum Press. NY, 1980, p. 365]. Control wells. where only the MNS-2 myeloma cells or only activated normal donor cells were placed, did not show any growth or Ig secretion under these conditions and were dead in less than 14 days.

4. Results

The frequency of hybridization under the experimental conditions (supra) may be expressed as the number of human Ig synthesizing hybridomas observed, per total cells in the reaction mixture (1/100,000), per MNS-2 (1/25,000), or less accurately, per activated B cells (estimated at 1/15,000). In the last instance, the estimate is based on the MNC population containing 73% T cells, of which the $T_H$ are considered important in the in vitro sensitization, 7% monocytes and 20% B cells to then yield the approximation of B cells. However, the actual number of activated B cells becomes less reliable (as the blastogenic Ig produced can only given an approximation of the actual numbers sensitized), but this fusion ratio then is probably a conservative one. Fusion frequency expressed as the yield of clones producing a specific Monoclonal antibody (MoAb) is much less, of course. Nonetheless, it is evident that using the in vitro antigen sensitized preparations, the relative frequency of fusion is high and, since Ig secretion is seen by day 12 following fusion, early cloning is useful.

Two Clones, #Ru26 and Ru70 yielded TC supernatants at day 22 with a Rubizyme ® (ELISA) index of 0.251 and 0.754, respectively, indicating the presence of an antirubella MoAb. 96 other clones producing Ig were negative. The index of 0.754 is approximately equivalent to a hemagglutination inhibition titer of 1:8. Both clones, Ru26 and Ru70, have been recloned and are growing preparatory for batch cultures and further study of the anti-rubella MoAb.

Having now fully described this invention, it will be apparent to those of skill in this art that the same can be practiced within a variety of equivalent process and composition parameters without affecting the spirit or scope of the invention or any embodiments thereof.

What is claimed as new and intended to be covered by Letters Patent of the United States is:

1. A biologically pure cell culture comprising a continuous human, non-immunoglobulin-secreting $HPRT^-$ plasmacytoid cell line having ATCC Deposit Number CRL-8147 and clones or subclones thereof.

2. A method of producing a human-human hybridoma which comprises:
   fusing an antibody producing human B-lymphocyte with the non-secretory human plasmacytoma of claim 1 to thereby form an antibody-producing hybridoma; and
   selecting for said hybridoma in HAT media.

3. A method of producing human-human hybridomas which comprises:

fusing an antibody producing human B-lymphocyte with the non-secretory HPRT-human plasmacytoma of claim 1 to form an antibody-producing hybridoma;

mixing the resulting reaction mixture with fluorescent-labeled antibodies thereby allowing said fluorescent labeled antibodies to bind to said hybridoma;

and separating said hybridoma complexed with said fluorescent antibodies from said non-secretory human plasmacytoma by fluorescence activated cell sorting.

4. The method of claim 2 which also comprises admixing the reaction mixture containing the fused hybridoma and the non-secretory plasmacytoma with fluorescent-labeled antibodies thereby allowing said antibodies to bind to said hybridoma and;

separating said non-secretory human plasmacytoma from said hybridoma carrying said fluorescent antibodies by fluorescence activated cell sorting.

5. The method of claim 3 wherein the separation by fluorescence activated cell sorting is carried out prior to the selection in HAT media.

6. A hybridoma derived by fusion of the plasmacytoma of claim 1 with a human antibody-producing B lymphocyte.

7. The hybridoma of claim 6 wherein said B lymphocyte is peripheral, nodal or splenic.

8. The hybridoma of claim 6 which produces monoclonal antibodies having specificity against an agent which is infectious to humans.

9. The hybridoma of claim 8 wherein said agent is a virus or a bacterium.

* * * * *